United States Patent
Schöttle et al.

[11] Patent Number: 5,129,997
[45] Date of Patent: Jul. 14, 1992

[54] PROCESS FOR THE RECOVERY OF MIXTURES OF CHLOROTETRAFLUOROETHANE AND OCTAFLUOROCYCLOBUTANE

[75] Inventors: Thomas Schöttle, Burghausen; Herbert Weber, Burgkirchen; Werner Dostler, Mettenheim-Hart; Karl Rettenbeck, Burgkirchen, all of Fed. Rep. of Germany

[73] Assignee: Hoechst Aktiengesellschaft, Frankfurt am Main, Fed. Rep. of Germany

[21] Appl. No.: 683,238

[22] Filed: Apr. 10, 1991

[30] Foreign Application Priority Data

Apr. 12, 1990 [DE] Fed. Rep. of Germany ....... 4011820

[51] Int. Cl.$^5$ .................... B01D 3/14; C07C 17/38
[52] U.S. Cl. ................... 203/99; 203/DIG. 9; 203/DIG. 19; 570/178
[58] Field of Search ................ 203/99, DIG. 19, 67, 203/69, DIG. 9; 570/178

[56] References Cited

U.S. PATENT DOCUMENTS

| 2,406,794 | 9/1946 | Benning et al. | 570/178 |
| 2,640,017 | 5/1953 | Graff | 203/99 |
| 3,408,264 | 10/1968 | Ward | 203/99 |
| 4,623,432 | 11/1986 | Ali | 203/DIG. 19 |
| 4,747,914 | 5/1988 | Schwarzmaier et al. | 203/DIG. 9 |
| 4,898,645 | 2/1990 | Voight et al. | 570/178 |

FOREIGN PATENT DOCUMENTS

| 0337127 | 10/1989 | European Pat. Off. | |
| 1587727 | 4/1981 | United Kingdom | 203/DIG. 19 |

OTHER PUBLICATIONS

R. J. Hengstebeck: *Distillation; Principles & Design Procedures*, Reinhold Publ. Corp. N.Y., 1961 (pp. 119, 147 and 193).

*Primary Examiner*—Wilbur Bascomb, Jr.

[57] ABSTRACT

A process for the preparation of mixtures of chlorotetrafluoroethane and octafluorocyclobutane from the gas stream from the pyrolysis of chlorodifluoromethane at temperatures above 600° C. is described in which the principal constituents tetrafluoroethylene and hexafluoropropylene as well as hydrogen chloride are removed in advance. The mixtures are obtained by withdrawal as a side fraction during the rectifying distillation of the residue remaining, a clean separation of the perfluorocyclobutenes advantageously taking place. The mixtures are used for obtaining hexafluoropropylene by pyrolysis.

5 Claims, No Drawings

PROCESS FOR THE RECOVERY OF MIXTURES OF CHLOROTETRAFLUOROETHANE AND OCTAFLUOROCYCLOBUTANE

DESCRIPTION

The invention relates to a process for the preparation of mixtures of chlorotetrafluoroethane and octafluorocyclobutane from the gas stream from the pyrolysis of chlorodifluoromethane at temperatures above 600° C., from which the main amount of hydrogen chloride, tetrafluoroethylene (TFE), hexafluoropropylene (HFP) and unreacted chlorodifluoromethane have already been removed, by distillation of the remaining constituents in a rectifying column.

It is known, for example from U.S. Pat. No. 2,551,573, that in the pyrolysis of chlorodifluoromethane at temperatures above 600° C., in addition to the principal product TFE and in addition to hydrogen chloride, still other fluoroalkanes and chlorofluoroalkanes, -cycloalkanes and -alkenes are formed, such as, for example, HFP, octafluorocyclobutane, chlorotetrafluoroethane, chlorohexafluoropropane, chlorotrifluoroethylene, dichlorodifluoromethane and the isomeric perfluorobutenes. Still other compounds are additionally formed, which have a higher boiling point than the highest-boiling of the compounds mentioned, namely chlorohexafluoropropane. The perfluoroalkenes TFE and HFP have great importance for the preparation of corresponding fluoropolymers and of copolymers from these monomers. Octafluorocyclobutane and chlorotetrafluoroethane and in particular mixtures of these two substances are starting materials for the pyrolytic preparation of HFP, in particular according to a process with the addition of tetrafluoroethylene, as is described in EP-OS 337,127.

The main amounts of the principal product TFE, of the hydrogen chloride formed and of the unreacted starting material chlorodifluoromethane are first removed from the gas stream from the pyrolysis of chlorodifluoromethane, which is carried out at temperatures of 600° C. and above, together with all compounds which boil at a lower temperature than chlorodifluoromethane (b.p. −40.8° C.). In the distillative separation of the remaining product mixture, first the compounds which boil at a higher temperature than chlorohexafluoropropane (i.e. with boiling points > +20° C.) are removed at the foot of the column by a process such as is described in U.S. Pat. No. 3,101,304. The amount leaving this column over the top, which essentially contains HFP, octafluorocyclobutane, chlorotetrafluoroethane, chlorohexafluoropropane, chlorotrifluoroethylene and dichlorodifluoromethane, is fed to an extractive rectification. Aromatic hydrocarbons and halogen-containing aliphatic and aromatic hydrocarbons are employed as extracting agents. Mineral oils are also suitable (U.S. Pat. No. 2,384,449). In this process, HFP and octafluorocyclobutane are led off over the top of this column as a mixture whose separation requires a further column. A mixture of essentially chlorotetrafluoroethane, chlorohexafluoropropane, chlorotrifluoroethylene and dichlorodifluoromethane together with the extracting agent remains in the bottom product of this process. The latter is removed in an additional rectifying column. The further separation of this fraction containing the chlorotetrafluoroethane is not described.

The object was therefore to develop a simple process for the recovery of mixtures of chlorotetrafluoroethane and octafluorocyclobutane, in which the outlay in terms of apparatus can in particular be reduced.

According to the present invention, this is achieved by a process of the type mentioned at the beginning, which comprises withdrawing a mixture of chlorotetrafluoroethane and octafluorocyclobutane from the rectifying column as a side fraction, the withdrawal of the side fraction being carried out in a region of the rectifying column which includes 5 to 90% of its total length, calculated from the top of the column, and the perfluorobutenes and the compounds which boil at a higher temperature than the perfluorobutenes remaining in the bottom of the rectifying column and the compounds which boil at a lower temperature than chlorotetrafluoroethane being led off over the top.

The starting material, which is treated according to the process of the present invention, is the gas stream from the pyrolysis of chlorodifluoromethane, which is carried out at a temperature above 600° C., the desired principal product TFE, the hydrogen chloride produced during the pyrolysis and additionally HFP, the starting material chlorodifluoromethane and the compounds which boil at a lower temperature than chlorodifluoromethane previously having been removed from this gas stream by distillation according to known processes. This starting mixture accordingly contains chlorotetrafluoroethane, octafluorocyclobutane, chlorotrifluoroethylene, dichlorodifluoromethane, the perfluorobutenes, chlorohexafluoropropane and smaller amounts of other compounds which boil at a higher temperature than chlorohexafluoropropane.

"Perfluorobutenes" here should be understood as meaning the two perfluorobutene isomers perfluorobut-1-ene and perfluorobut-2-ene, which may optionally also contain some perfluoroisobutylene. "Chlorotetrafluoroethane" is to be understood as meaning both 1-chloro-1,1,2- and 1-chloro-1,2,2,2-tetrafluoroethane isomers, the first isomer usually being found as the main constituent.

If desired, still other gases which essentially comprise chlorotetrafluoroethane or octafluorocyclobutane or mixtures of these two gases can be admixed to this starting mixture.

This starting mixture is fed to a rectifying column which is equipped with a device which permits the withdrawal of a side fraction. In order to ensure an adequate separating effect, this device should be in the region from 5 to 90% of the total length of the column, calculated from the top of the column, preferably in such a region from 20 to 70%.

The feeding-in to the rectifying column takes place, as is customary, from the side and should be in the same region of the column as the withdrawal. The feeding-in preferably takes place at the same height as or below the withdrawal of the side fraction.

The pressure in the rectifying column is atmospheric pressure or above and can vary within wide limits. Expediently it is kept, when using water as the cooling agent, at 6 to 8 bar.

The mixture withdrawn as the side fraction of the rectifying column has a composition of chlorotetrafluoroethane:octafluorocyclobutane in the range from 1:10 to 10:1 parts by weight, preferably in the range from 1:4 to 4:1 part by weight.

The mixture led off over the top of the column contains the compounds which boil at a lower temperature than chlorotetrafluoroethane, in particular chlorotrifluoroethylene and dichlorodifluoromethane. The perfluorobutenes, in particular, are found in the bottom of the rectifying column in addition to chlorohexafluoropropane and compounds which boil at a higher temperature than chlorohexafluoropropane The process according to the invention initially brings with it a considerable advantage in terms of apparatus, as the constituents chlorotetrafluoroethane and octafluorocyclobutane are obtained directly in the mixture and do not have to be separated from other constituents or from the extracting agent in separate steps.

In addition, the difficult separation, by extractive distillation, of the perfluorobutenes which remain with the octafluorocyclobutane, is possible here without problems. As, in the process according to the invention, octafluorocyclobutane and chlorotetrafluoroethane are present in the mixture and this mixture has an azeotropic point with a boiling point minimum, their relative volatility compared to that of the perfluorobutenes is increased as a result and thus their separation is considerably improved.

The invention is illustrated by the following examples:

EXAMPLE 1

A packed column (42 plates) of 21.4 m length and 0.3 m diameter operated at 7.5 bar is continuously charged with 112.03 kg/h of a mixture which contains the following components:

|  | % by weight |
|---|---|
| Dichlorodifluoromethane | 0.43 |
| Chlorotrifluoroethylene | 1.29 |
| Residue 1* | 1.88 |
| Octafluorocyclobutane | 52.99 |
| Chlorotetrafluoroethane | 22.83 |
| Perfluorobut-2-ene | 2.22 |
| Perfluorobut-1-ene |  |
| Chlorohexafluoropropane | 12.50 |
| Residue 2** | 5.85 |

*Residue 1: Substances which boil at a lower temperature than chlorotetrafluoroethane
**Residue 2: Substances which boil at a higher temperature than the perfluorobutenes The starting mixture is fed in at a point 83.4% of the length of the column below the top. The reflux ratio is 1:10 with respect to the feed to the column. The temperature of the column reaches from 37° C. at the top to 95° C. at the foot of the column.

The withdrawal of the side fraction, which mainly contains octafluorocyclobutane and chlorotetrafluoroethane, is carried out at a point 51.4% of the length of the column below the top of the column at a rate of 86.76 kg/h. It has the following composition:

|  | % by weight |
|---|---|
| Dichlorodifluoromethane | 0.13 |
| Chlorotrifluoroethylene | 0.13 |
| Residue 1* | 0.63 |
| Octafluorocyclobutane | 67.70 |
| Chlorotetrafluoroethane | 29.29 |
| Perfluorobut-2-ene | 1.87 |
| Perfluorobut-1-ene |  |
| Chlorohexafluoropropane | 0 |
| Residue 2** | 0.25 |

The side fraction contains 98% by weight of the amount of octafluorocyclobutane and 99.3% by weight of the amount of chlorotetrafluoroethane, relative to the amount added in the starting mixture.

EXAMPLE 2

The packed column described in Example 1 and equipped with the same feed is used. The withdrawal of the side fraction is carried out at a point 39% of the length of the column below the top of the column. The column is operated at a temperature of 37.5° C. at the foot and 93° C. at the top, and the reflux ratio is again 1:10. 124.07 kg/h of a mixture of the following composition are continuously fed in:

|  | % by weight |
|---|---|
| Dichlorodifluoromethane | 0.41 |
| Chlorotrifluoroethylene | 1.64 |
| Residue 1* | 2.10 |
| Octafluorocyclobutane | 28.23 |
| Chlorotetrafluoroethane | 45.06 |
| Perfluorobut-2-ene | 2.93 |
| Perfluorobut-1-ene |  |
| Chlorohexafluoropropane | 11.28 |
| Residue 2** | 8.34 |

*Residue 1: Substances which boil at a lower temperature than chlorotetrafluoroethane
**Residue 2: Substances which boil at a higher temperature than the perfluorobutenes 92.2 kg/h Of a mixture of the following composition are removed as a side fraction:

|  | % by weight |
|---|---|
| Dichlorodifluoromethane | 0.18 |
| Chlorotrifluoroethylene | 0.18 |
| Residue 1* | 0.89 |
| Octafluorocyclobutane | 37.07 |
| Chlorotetrafluoroethane | 60.09 |
| Perfluorobut-2-ene | 1.46 |
| Perfluorobut-1-ene |  |
| Chlorohexafluoropropane | 0 |
| Residue 2** | 0.13 |

The side fraction contains 97.1% by weight of the amount of octafluorocyclobutane and 99.1% by weight of the amount of chlorotetrafluoroethane, relative to the amount added in the starting mixture.

We claim:

1. A process for recovering mixtures of chlorotetrafluoroethane and octafluorocyclobutane from pyrolysis products of chlorodifluoromethane, wherein the pyrolysis has been conducted at a temperature above 600° C., and wherein hydrogen chloride, tetrafluoroethylene, hexafluoropropylene and unreacted chlorodifluoromethane have been substantially removed from the pyrolysis products, said process comprising:

distilling in a rectifying column the remaining pyrolysis products, which remaining pyrolysis products comprise chlorotetrafluoroethane, octafluorocyclobutane, perfluorobutenes, compounds which boil at a temperature higher than the perfluorbutenes, and compounds which boil at a lower temperature than chlorotetrafluoroethane, and withdrawing a mixture of chlorotetrafluoroethane and octafluorocyclobutane from the rectifying column as a side fraction, the withdrawal of the side fraction being carried out in a region of the rectifying column which includes 5 to 90% of its total length, calculated from the top of the column, the perfluorobutenes and the compounds which boil at a higher temperature than the perfluorobutenes remaining in a bottom product withdrawn from the rectifying column, and the compounds which boil at a lower temperature than chlorotetrafluoroethane being included in a top product withdrawn from the rectifying column 2. The process for recovering mixtures of chlorotetrafluoroethane and octafluorocyclobutane as claimed in claim 1, wherein the withdrawal of the side fraction takes place in a region of the rectifying column which includes 20 to 70% of its total length, calculated from the top of the column.

3. The process for recovering mixtures of chlorotetrafluoroethane and octafluorocyclobutane as claimed in claim 1, wherein other gases which comprise chlorotetrafluoroethane or octafluorocyclobutane or mixtures of these two gases are admixed to the remaining pyrolysis products.

4. The process for recovering mixtures of chlorotetrafluoroethane and octafluorocyclobutane as claimed in claim 1, wherein the side fraction withdrawn has a composition of chlorotetrafluoroethane:octafluorocyclobutane in the range from 1:10 to 10:1 parts by weight.

5. The process for recovering mixtures of chlorotetrafluoroethane and octafluorocyclobutane as claimed in claim 1, wherein the side fraction withdrawn has a composition of chlorotetrafluoroethane:octafluorocyclobutane in the range from 1:4 to 4:1 parts by weight.

* * * * *